(12) United States Patent
Dou et al.

(10) Patent No.: US 8,748,670 B1
(45) Date of Patent: Jun. 10, 2014

(54) HIGHLY ACTIVE OXIDE CATALYSTS FOR THE CATALYTIC KETONIZATION OF CARBOXYLIC ACIDS

(71) Applicant: Massachusetts Institute of Technology, Cambridge, MA (US)

(72) Inventors: Herui Dou, Zhejiang (CN); Yuriy Roman-Leshkov, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/836,570

(22) Filed: Mar. 15, 2013

(51) Int. Cl.
*C07C 45/00* (2006.01)
(52) U.S. Cl.
USPC ............................................. 568/397
(58) Field of Classification Search
USPC ............................................. 568/397
See application file for complete search history.

(56) References Cited

U.S. PATENT DOCUMENTS 4,172,097 A 10/1979 Smith et al.

OTHER PUBLICATIONS

Afzal et al., Kinetics of Thermal Decomposition of Metal Acetates, Journal of Thermal Analysis, 37:1015-1023 (1991).
Arabaci A. et al., Characterization of thermal decomposition products of cerium acetate by high temperature FTIR spectroscopy, Ceram. Mater., 62(3):294-296 (2010).
Arii, T. et al., Thermal decomposition of cerium (III) acetate hydrate by a three-dimensional thermal analysis, Japan Society for Analytical Chemistry, 17:875-880 (2001).
Arii, T. et al., Thermal decomposition of cerium (III) acetate studied with sample-controlled thermogravimetric-mass spectrometry (SCTG-MS), Journal of European Ceramic Society, 22:2283-2289 (2002).
Christensen, C.H. et al., The renewable chemicals industry, ChemSusChem, 1:283-289 (2008).
Gaertner C.A. et al., Ketonization reactions of carboxylic acids and esters over ceria-zirconia as biomass-upgrading processes, Ind. Eng. Chem. Res., 49:6027-6033 (2010).
Gaertner, C.A. et al., Catalytic coupling of carboxylic acids by ketonization as a processing step in biomass conversion, J. Catal., 266:71-78 (2009).
Gaertner, C.A. et al., Catalytic upgrading of bio-oils by ketonization, ChemSusChem 2:1121-1124 (2009).
Glinski M. et al., Catalytic ketonization over oxide catalysts x. Transformations of various alkyl heptanoates, Appl. Catal. A, 281:107-113 (2005).
Glinski, M. et al., Catalytic ketonization of carboxylic acids synthesis of saturated and unsaturated ketones, React. Kinet. Catal. Lett., 69(1):123-128 (2000).
Glinski, M. et al., Ketones from monocarboxylic acids; catalytic ketonization over oxide systems, Appl. Catal. A, 128:209-217 (1995).
Gooβen, L.J. et al., Catalytic decarboxylative cross-ketonisation of aryl- and alkyl-carboxylic acids using magnetite nanoparticles, Adv. Synth. Catal., 353:57-63 (2011).
Ibrahim, M. et al., Density functional theory and FTIR spectroscopic study of carboxyl group, Ind. J. Pure Appl. Phy., 43:911-917 (2005).
Jones, L.H., Infrared spectra and structure of the crystalline sodium acetate complexes of U(VI), Np(VI), Pu(VI), and Am(VI). A comparison of metal oxygen bond distance and bond force constant in this series, J. Chem. Phy., 23:2105-2107 (1955).
Kunkes, E.L., et al., Catalytic conversion of biomass to monofunctional hydrocarbons and targeted liquid-fuel classes, Science, 322, 417-421 (2008).
Nagashima O. et al., Ketonization of carboxylic acids over CeO2-based composite oxides, J. Mol. Catal. A, 227:231-239 (2005).
Pestman R. et al., The formation of ketones and aldehydes from carboxylic acids, structure-activity relationship for two competitive reactions, J. Mol. Catal. A, 103:175-180 (1955).
Rand L. et al., Reactions catalyzed by potassium fluoride. II. The conversion of adipic acid to cyclo-pentanone, J. Org. Chem., 27:1034-1035 (1962).
Renz, M., Ketonization of carboxylic acids by decarboxylation: mechanism and scope, Eur. J. Org. Chem., 979-988 (2005).
Vlase, T. et al., About compensation effect by thermal decomposition of some catalyst precursors, J. Therm. Anal. Calorim., 80:87-90 (2005).

*Primary Examiner* — Sikarl Witherspoon
(74) *Attorney, Agent, or Firm* — Choate, Hall & Stewart, LLP; Andrea L. C. Robidoux; Xiaodong Li

(57) ABSTRACT

The present invention provides methods comprising reacting a first carboxylic acid or ester with a second carboxylic acid or ester in the presence of a metal oxide comprising Zr, Ce, Mn and O to produce at least one ketone.

20 Claims, 12 Drawing Sheets

HIGHLY ACTIVE OXIDE CATALYSTS FOR THE CATALYTIC KETONIZATION OF CARBOXYLIC ACIDS

FIELD OF THE INVENTION

The present invention generally relates to catalytic conversion of carboxylic acids or esters into ketones.

BACKGROUND

Carboxylic acids and/or esters are major components in biomass and/or bio-oils. Bio-oils typically contain a signification quantity (up to 30 wt %) of carboxylic acids, which provides these liquids with high acidity and corrosiveness. The high reactivity of acids leads to instability of the bio-oil. These undesired properties, along with the high amount of hydrogen consumed by carboxylic acids during hydrodeoxygenation to hydrocarbons, make it necessary to develop techniques for effective removal of acids from bio-oils. The conversion of carboxylic acids and/or esters to compounds with low oxygen content, such as ketones, is an important chemical process that adds commercial value to biomass and/or bio-oil. One reaction for this conversion, ketonization, which converts carboxylic acids or esters into ketones by decarboxylation, is useful for the production of symmetric and non-symmetric ketones. Catalytic ketonization in an important method for ketone production and upgrading of fuels, including but not limited to bio-oils, by increasing the heating value and stability. The utilization of biomass to produce fuels comprising the conversion of carboxylic acids and/or esters into ketones is a promising way to sustainably produce clean energy and alleviate our societal and economic dependence on fossil fuels.

Catalytic ketonization by metal oxides has been reported. The known methods require high temperature and/or high pressure which lead to many problems, including but not limited to undersirable phase transformations of the catalysts and increased reactor pressure drop. When the feed composition comprises components other than carboxylic acids (or esters) to be converted, unwanted reactions can happen to the other components, which need to be minimized or avoided especially in the upgrading of bio-oils.

SUMMARY

Figure 1:
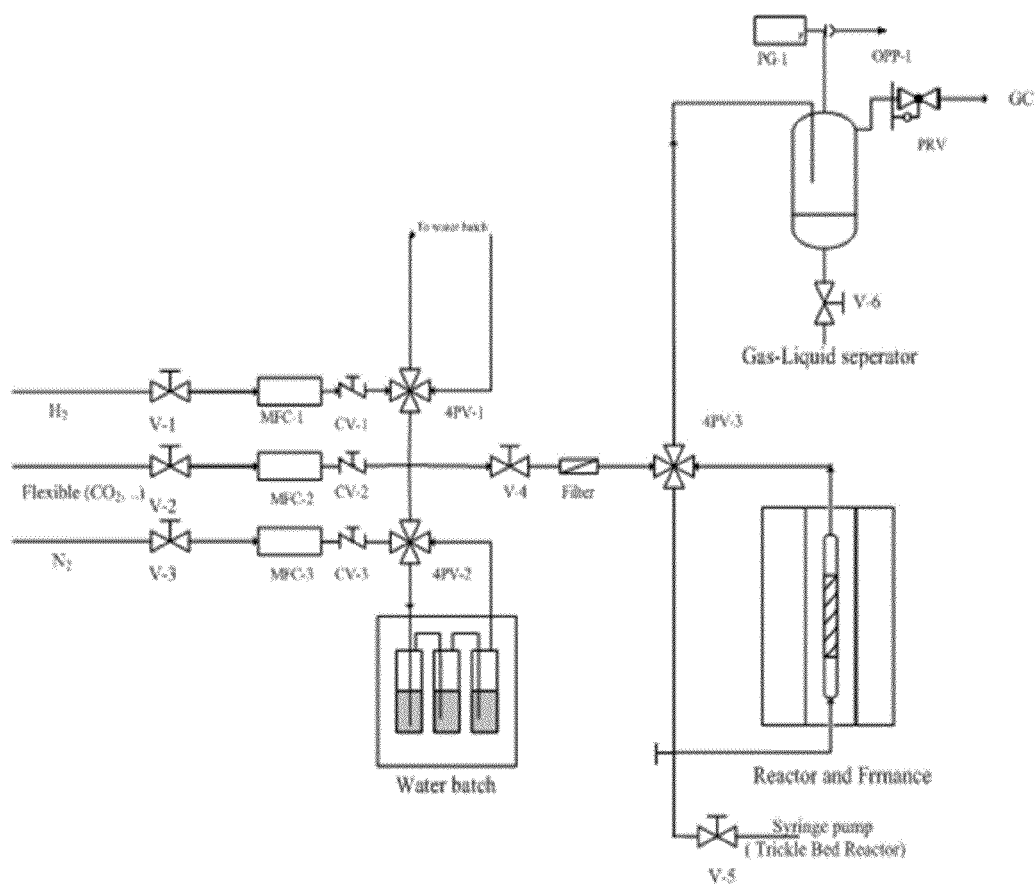
FIG. 1. Diagram of the Plug-Flow Reactor for ketonization reaction

In some embodiments, the present invention recognizes the challenges and problems faced by prior ketonization methods, including but not limited to high temperature, high pressure, low flow rate, unstable catalyst, undesirable reactor pressure drop and side reactions. In some embodiments, the present invention provides a method, comprising reacting a first carboxylic acid or ester with a second carboxylic acid or ester in the presence of a metal oxide comprising Zr, Mn and O to produce at least one ketone. In some embodiments, the present invention provides a method, comprising reacting a first carboxylic acid or ester with a second carboxylic acid or ester in the presence of a metal oxide comprising Zr, Ce, Mn and O to produce at least one ketone. In some embodiments, the at least one ketone is produced through ketonization of the first or second carboxylic acids or esters.

DETAILED DESCRIPTION OF CERTAIN EMBODIMENTS

1. General Description of Certain Embodiments of the Invention

In some embodiments, the present invention provides a method, comprising reacting a first carboxylic acid or ester with a second carboxylic acid or ester in the presence of a metal oxide comprising Zr, Mn and O to produce at least one ketone. In some embodiments, the present invention provides a method, comprising reacting a first carboxylic acid or ester with a second carboxylic acid or ester in the presence of a metal oxide comprising Zr, Ce, Mn and O to produce at least one ketone. In some embodiments, the present invention provides a method, comprising reacting a first carboxylic acid with a second carboxylic acid in the presence of a metal oxide comprising Zr, Mn and O to produce at least one ketone. In some embodiments, the present invention provides a method, comprising reacting a first carboxylic acid with a second carboxylic acid in the presence of a metal oxide comprising Zr, Ce, Mn and O to produce at least one ketone. In some embodiments, the present invention provides a method, comprising reacting a first ester with a second ester in the presence of a metal oxide comprising Zr, Mn and O to produce at least one ketone. In some embodiments, the present invention provides a method, comprising reacting a first ester with a second ester in the presence of a metal oxide comprising Zr, Ce, Mn and O to produce at least one ketone. In some embodiments, the present invention provides a method for performing ketonization, comprising reacting the ketonization substrates in the presence of a metal oxide comprising Zr, Mn and O. In some embodiments, the present invention provides a method for performing ketonization, comprising reacting the ketonization substrates in the presence of a metal oxide comprising Zr, Ce, Mn and O.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly (ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1, 4-oxazin-3(4H)-one. A heteroaryl group may be monocyclic, bicyclic, tricyclic, tetracyclic, and/or otherwise polycyclic The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —(CH$_2$)$_{0-4}$SR$^\circ$; —(CH$_2$)$_{0-4}$S(O)R$^\circ$; —(CH$_2$)$_{0-4}$S(O)$_2$R$^\circ$; —O(CH$_2$)$_{0-4}$R$^\circ$, —O—(CH$_2$)$_{0-4}$C(O)OR$^\circ$; —(CH$_2$)$_{0-4}$—CH(OR$_2$); —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(RO$_2$); —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NRO$_2$; —N(R$^\circ$)C(S)NRO$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NRO$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NRO$_2$; —C(S)NRO$_2$; —C(S)SR$^\circ$; —SC(S)SR$^\circ$, —(CH$_2$)$_{0-4}$OC(O)NRO$_2$; —C(O)N(OR$^\circ$)R$^\circ$; —C(O)C(O)R$^\circ$; —C(O)(CH$_2$)C(O)R$^\circ$; —C(NOR$^\circ$R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NRO$_2$; —(CH$_2$)$_{0-4}$S(O)R$^\circ$; —N(R$^\circ$)S(O)$_2$NRO$_2$; —N(R$^\circ$)S(O)$_2$R$^\circ$; —N(OR$^\circ$)R$^\circ$; —C(NH)NRO$_2$; —P(O)$_2$R$^\circ$; —P(O)RO$_2$; —OP(O)RO$_2$; —OP(O)(ORO$_2$); —PRO$_2$; —OPRO$_2$; —SiR$^\circ_3$; —OSiR$^\circ_3$; —(C$_{1-4}$ straight or branched)alkylene)O—N(RO$_2$; or —(C$_{1-4}$ straight or branched) alkylene)C(O)O—N(RO$_2$; wherein each R$^\circ$ may be substituted as defined below and is independently hydrogen, C$_{1-6}$aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-30}$—, or —S(C(R*$_2$))$_{2-35}$—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, —(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R˙, —(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C— or $^{13}$C— or $^{14}$C-enriched carbon are within the scope of this invention. Such compounds are useful, for example, as analytical tools or probes in biological assays.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

As used herein and in the claims, the singular forms "a", "an", and "the" include the plural reference unless the context clearly indicates otherwise. Thus, for example, a reference to "a compound" includes a plurality of such compounds.

The term "carboxylic acid" is given its ordinary meaning in the art and refers to a compound comprising the —C(=O) OH group, and the term "ester" refers a compound derived from an carboxylic acid and an alcohol by linking with formal loss of water from the hydroxyl group of the —CO(=O)OH group in the former and a hydroxy group of the latter. In some embodiments, the alcohol is optionally substituted phenol. In some embodiments, the alcohol is heteroarenol. In some embodiments, the alcohol is enol. In some embodiments, the alcohol is an aliphatic alcohol, wherein the hydroxyl group is connected to an optionally substituted aliphatic group.

The term "ketonization", as used herein, refers to a reaction between two carboxylic acids or esters to form a ketone. In some embodiments, water and carbon dioxide are also formed as the products. In some embodiments, the ketonization reaction is between two carboxylic acids. In some embodiments, the ketonization reaction is between two esters.

3. Description of Certain Embodiments of the Invention

As generally defined above, in some embodiments, the present invention provides a method, comprising reacting a first carboxylic acid or ester with a second carboxylic acid or ester in the presence of a metal oxide comprising Zr, Mn and O to produce at least one ketone. In some embodiments, the present invention provides a method, comprising reacting a first carboxylic acid or ester with a second carboxylic acid or ester in the presence of a metal oxide comprising Zr, Ce, Mn and O to produce at least one ketone. In some embodiments, the present invention provides a method, comprising reacting a first carboxylic acid with a second carboxylic acid in the presence of a metal oxide comprising Zr, Mn and O to produce at least one ketone. In some embodiments, the present invention provides a method, comprising reacting a first carboxylic acid with a second carboxylic acid in the presence of a metal oxide comprising Zr, Ce, Mn and O to produce at least one ketone. In some embodiments, the present invention provides a method, comprising reacting a first ester with a second ester in the presence of a metal oxide comprising Zr, Mn and O to produce at least one ketone. In some embodiments, the present invention provides a method, comprising reacting a first ester with a second ester in the presence of a metal oxide comprising Zr, Ce, Mn and O to produce at least one ketone. In some embodiments, the present invention provides a method for performing ketonization, comprising reacting the ketonization substrates in the presence of a metal oxide comprising Zr, Mn and O. In some embodiments, the present invention provides a method for performing ketonization, comprising reacting the ketonization substrates in the presence of a metal oxide comprising Zr, Ce, Mn and O. In some embodiments, the ketonization substrates are carboxylic acids. In some other embodiments, the ketonization substrates are esters.

In some embodiments, the first carboxylic acid or ester is the same as the second carboxylic acid or ester. In some embodiments, the first carboxylic acid is the same as the second carboxylic acid. In some embodiments, the first ester is the same as the second ester.

It is understood by a person of ordinary skill in the art that carboxylic acid or ester of various structures can be used in a provided method. In some embodiments, a carboxylic acid in a provided method has the structure of RCOOH, wherein R is an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, an ester in a provided method has the structure of RCOOR, wherein each R is independently as defined above and described herein.

In some embodiments, R is optionally substituted $C_{1-20}$ aliphatic. In some embodiments, R is optionally substituted $C_{1-12}$ aliphatic. In some embodiments, R is optionally substituted $C_{1-10}$ aliphatic. In some embodiments, R is optionally substituted $C_{1-8}$ aliphatic. In some embodiments, R is optionally substituted $C_{1-6}$ aliphatic. In some embodiments, R is optionally substituted $C_{1-4}$ aliphatic. In some embodiments, R is optionally substituted $C_{1-2}$ aliphatic. In some embodiments, the carboxylic acid is acetic acid. In some embodiments, the carboxylic acid is propanoic acid. In some embodiments, RCOOH is a diacid or polyacid, wherein the R group comprises one or more —COOH substituents.

In some embodiments, an acid or ester in a provided method is from a biomass. In some embodiments, an acid in a provided method is from a biomass. In some embodiments, an ester in a provided method is from a biomass. In some embodiments, an acid or ester is derived from a sugar. In some embodiments, an acid is a four carbon 1,4-diacid. In some embodiments, the acid is 2,5-furan dicarboxylic acid. In some embodiments, the acid is 3-hydroxpropionic acid. In some embodiments, the acid is aspartic acid, glucaric acid, glutamic acid, itaconic acid or levulinic acid. In some embodiments, the acid is a $C_4$ to $C_6$ acid. In some embodiments, the acid is pentanoic acid. In some embodiments, an acid or ester in a provided method is from a fuel. In some embodiments, an acid in a provided method is from a fuel. In some embodiments, an ester in a provided method is from a fuel. In some embodiments, an acid or ester in a provided method is from a bio-fuel. In some embodiments, an acid in a provided method is from a bio-fuel. In some embodiments, an ester in a provided method is from a biofuel. In some embodiments, an acid or ester in a provided method is from a bio-oil. In some embodiments, an acid in a provided method is from a bio-oil. In some embodiments, an ester in a provided method is from a bio-oil.

In some embodiments, a provided method does not need the substrates, i.e., the carboxylic acids or esters, to be in a purified form. Carboxylic acids or esters that are components of a mixture can be used in the provided methods. In some embodiments, the first carboxylic acid or ester and the second carboxylic acid or ester are components of a composition further comprising other compounds. In some embodiments, the first carboxylic acid and the second carboxylic acid are components of a composition further comprising other compounds. In some embodiments, the first ester and the second ester are components of a composition further comprising other compounds. In some embodiments, a composition comprising the first and the second carboxylic acid or ester is a biomass. In some embodiments, a composition comprising the first and the second carboxylic acid or ester is a fuel. In some embodiments, a composition comprising the first and the second carboxylic acid or ester is a biofuel. In some embodiments, a composition comprising the first and the second carboxylic acid or ester is a bio-oil. In some embodiments, a composition comprising the first and the second carboxylic acids is a bio-oil In some embodiments, the first carboxylic acid and the second carboxylic are the same. In some embodiments, each of the first and second carboxylic acid is a $C_n$ acid and the at least one ketone has 2n−1 carbon atoms, wherein n is an integer between 1 and 20, inclusive.

In some embodiments, the first carboxylic acid and the second carboxylic acid are different. In some embodiments, the first and second carboxylic acids together have m carbon atoms, and the at least one ketone has m−1 carbon atoms, wherein m is an integer between 1 and 40, inclusive.

In some embodiments, the first carboxylic acid or ester and the second carboxylic acid or ester are two —COOH or ester groups within the same molecule. In some embodiments, the first carboxylic acid and the second carboxylic acid are two —COOH groups within the same molecule. In some embodiments, the reaction between the first carboxylic acid or ester and the second carboxylic or ester is an intramolecular reaction between two —COOH or ester groups of the same molecule.

In some embodiments, a metal oxide in a provided method comprises Zr, Ce, Mn and o. In some embodiments, a metal oxide in a provided method consists of Zr, Ce, Mn and O. In some embodiments, the metal oxide has the structure of $Zr_wCe_xMn_yO_z$, wherein $2(w+x+y)=z$, x is 0 or a number greater than 0, and each of w, y and z is a number greater than 0. In some embodiments, the metal oxide has the structure of $Zr_wCe_xMn_yO_z$, wherein $2(w+x+y)=z$, and each of w, x, y and z is a number greater than 0. In some embodiments, Zr, Ce and Mn in the metal oxide exist in a solid-phase solution.

In some embodiments, a metal oxide in a provide method has only Zr, Ce and Mn as the metal elements. Such metal oxides do not have any other metal elements other than Zr, Ce and Mn. Suitable metal oxides can have Zr, Ce and Mn in any ratios. In some embodiments, the percentage of Mn among the metals (i.e., $y/(w+x+y)$) is greater than about 5%. In some embodiments, $y/(w+x+y)$ is greater than about 10%. In some embodiments, $y/(w+x+y)$ is greater than about 15%. In some embodiments, $y/(w+x+y)$ is greater than about 20%. In some embodiments, $y/(w+x+y)$ is greater than about 25%. In some embodiments, $y/(w+x+y)$ is greater than about 30%. In some embodiments, $y/(w+x+y)$ is greater than about 40%. In some embodiments, $y/(w+x+y)$ is greater than about 50%.

In some embodiments, the metal oxide is $Zr_{0.4}Ce_{0.4}Mn_{0.2}O_2$ (ZrCeMn-20). Unless otherwise specified, ZrCeMn-A, wherein A is an number greater than 0 and smaller than 100, refers to a metal oxide having the structure of $Zr_wCe_xMn_yO_z$, wherein $w=x=(1−A\%)/2$, $y=A\%$ and $z=2$. In some embodiments, the metal oxide is ZrCeMn-A, wherein A is greater than 0 and less than 100. In some embodiments, A is greater than about 5. In some embodiments, A is greater than about 10. In some embodiments, A is greater than about 15. In some embodiments, A is greater than about 20. In some embodiments, A is greater than about 25. In some embodiments, A is greater than about 30. In some embodiments, A is greater than about 40. In some embodiments, A is greater than about 50. In some embodiments, A is greater than about 60. In some embodiments, A is greater than about 70. In some embodiments, A is greater than about 80. In some embodiments, A is greater than about 90. In some embodiments, the metal oxide is ZrCeMn-5. In some embodiments, the metal oxide is ZrCeMn-10. In some embodiments, the metal oxide is ZrCeMn-20. In some embodiments, the metal oxide is ZrCeMn-40.

In some embodiments, a provided method is highly efficient. In some embodiments, the space velocity is about or greater than 10 $g_{feed} g_{cat}^{-1} h^{-1}$. In some embodiments, the space velocity is about 10 $g_{feed} g_{cat}^{-1} h^{-1}$. In some embodiments, the space velocity is greater about 10 $g_{feed} g_{cat}^{-1} h^{-1}$. In some embodiments, the space velocity is greater about 15 $g_{feed} g_{cat}^{-1} h^{-1}$. In some embodiments, a provided method converts acetic acid through ketonization reaction into acetone under about 350° C. and space velocities about 15 $g_{feed} g_{cat}^{-1} h^{-1}$. In some embodiments, a provided method converts propanoic acid through ketonization reaction into pentan-3-one under about 350° C. and space velocities about 15 $g_{feed} g_{cat}^{-1} h^{-1}$.

In some embodiments, a metal oxide in a provided method has a large surface. In some embodiments, the BET surface is greater than about 100 $m^2/g$.

In some embodiments, the metal oxide is partially converted to carbonate on the surface. In some embodiments, the metal oxide has a formula of $M_2O_zCO_3$, wherein M is Zr, Ce or Mn. In some embodiments, the metal oxide has a formula of $M_2O_2CO_3$, wherein M is Zr, Ce or Mn. In some embodiments, M is Zr. In some embodiments, M is Ce. In some embodiments, the metal oxide has a formula of $M_2O_2CO_3$, wherein M is Mn.

A metal oxide in a provided method can has various phases. In some embodiments, the metal oxide is tetragonal.

In some embodiments, a provided method maintains the structural integrity of the metal oxide. In some embodiments, a provided method maintains the structural integrity of the metal oxide, wherein the metal oxide has the structure of $Zr_wCe_xMn_yO_z$. In some embodiments, a provided method maintains the structural integrity of the metal oxide after about 30 hours and about 350° C. at the presence of the first and second carboxylic acids. In some embodiments, a provided method maintains the structural integrity of the metal oxide after about 30 hours and about 350° C., with both the first and second carboxylic acids being acetic acid. In some embodiments, a provided method maintains the morphology of the metal oxide. In some embodiments, a provided method maintains the morphology of the metal oxide, wherein the metal oxide has the structure of $Zr_wCe_xMn_yO_z$. In some embodiments, a provided method maintains the morphology of the metal oxide after about 30 hours and about 350° C. at the presence of the first and second carboxylic acids. In some embodiments, a provided method maintains the morphology of the metal oxide after about 30 hours and about 350° C., with both the first and second carboxylic acids being acetic acid. Maintenance of the structural integrity and/or morphology of the metal oxide bed can bring many benefits, including but not limited to extended catalyst (metal oxide) life and smaller reactor's pressure drop. In some embodiments, the structure of the metal oxide is characterized by PXRD. It is known that prior methods cannot maintain the structure integrity of the catalyst, often metal oxide bed. For example, some prior methods convert pellet CeMn-20 catalyst into very fine powder, which significantly increases the reactor's pressure drop, decreases the efficiency and/or shortens the life the catalyst bed. Methods provided in the present invention solve these problems.

In some embodiments, the ketone produced in a provided method is symmetric. In some embodiments, the first and the second carboxylic acids or esters are the same, and the ketone is symmetric. In some other embodiments, the ketone produced in a provided method is asymmetric. In some embodiments, the first carboxylic acid has the structure of $R^1COOH$, the second carboxylic acid has the structure of $R^2COOH$, and the ketone has the structure of $R^1C(O)R^2$, wherein each of $R^1$ and $R^2$ is independently R. In some embodiments, the first carboxylic acid has the structure of $R^1COOH$, the second carboxylic acid has the structure of $R^2COOH$, and the ketone has the structure of $R^1C(O)R^2$, wherein each of $R^1$ and $R^2$ is independently R. In some embodiments, $R^1$ of the ketone $R^1C(O)R^2$ is from the first carboxylic acid $R^1COOH$, and $R^2$ is from the second carboxylic acid $R^2COOH$. In some embodiments, each of $R^1COOH$ and $R^2COOH$ is independently an acid from a biomass. In some embodiments, each of $R^1COOH$ and $R^2COOH$ is independently an acid from a bio-oil. In some embodiments, each of $R^1COOH$ and $R^2COOH$ is independently an acid from a fuel. In some embodiments, each of $R^1COOH$ and $R^2COOH$ is independently an acid from a biofuel. In some embodiments, each of $R^1COOR^1$ and $R^2COOR^2$ is independently an ester from a biomass. In some embodiments, each of $R^1COOR^1$ and $R^2COOR^2$ is independently an ester from a bio-oil. In some embodiments, each of $R^1COOR^1$ and $R^2COOR^2$ is independently an ester from a fuel. In some embodiments, each of $R^1COOR^1$ and $R^2COOR^2$ is independently an ester from a biofuel.

In some embodiments, the ketonization reaction in a provided method is depicted in equation 1, below:

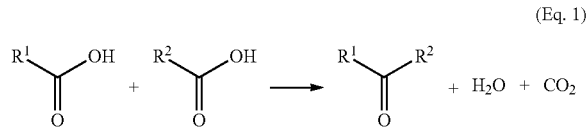

(Eq. 1)

In some embodiments, the ketone is produced through ketonization of the first and second carboxylic acids or esters. In some embodiments, the ketone is produced through ketonization of the first and second carboxylic acids.

As generally described above and here, in some embodiments, a provided method is particularly useful for upgrading a fuel. In some embodiments, a provided method further comprises the presence of one or more components found in a fuel. In some embodiments, a provided method is particularly useful for upgrading a bio-oil. In some embodiments, a provided method further comprises the presence of one or more components found in a bio-oil. In some embodiments, a provided method is particularly useful for upgrading a biofuel. In some embodiments, a provided method further comprises the presence of one or more components found in a biofuel. In some embodiments, the present invention provides a fuel upgrading method, comprising reacting a first carboxylic acid or ester with a second carboxylic acid or ester in the presence of a metal oxide comprising Zr, Mn and O to produce at least one ketone. In some embodiments, the present invention provides a fuel upgrading method, comprising reacting a first carboxylic acid or ester with a second carboxylic acid or ester in the presence of a metal oxide comprising Zr, Ce, Mn and O to produce at least one ketone.

In some embodiments, the present invention provides a biomass conversion process comprising reacting a first carboxylic acid or ester with a second carboxylic acid or ester in the presence of a metal oxide comprising Zr, Mn and O to produce at least one ketone. In some embodiments, the present invention provides a biomass conversion process comprising reacting a first carboxylic acid or ester with a second carboxylic acid or ester in the presence of a metal oxide comprising Zr, Ce, Mn and O to produce at least one ketone. In some embodiments, at least one product of the process is a fuel. In some embodiments, acids and/or esters in the biomass are converted to chemicals of increased value.

The high efficiency of the provided methods, especially at lower temperatures and/or pressure compared to those used in the prior art, is particularly important for processing biomass, fuel, biofuel and/or bio-oil, which comprises many other components besides the carboxylic acids or esters for ketonization. The provided mild conditions minimize or prevent undesirable side reactions between the many other components, and/or between them and the carboxylic acids or esters for ketonization.

Conditions

In some embodiments, the first and second carboxylic acids or esters are provided in gas phase. In some embodiments, the first and second carboxylic acids or esters are provided in liquid phase. In some embodiments, the first and second carboxylic acids or esters are provided in liquid phase. In some embodiments, the first and second carboxylic acids or esters are supplied as components of a feed composition comprising other compounds. Exemplary such feed compositions include but are not limited to bio-mass, fuel, biofuel and bio-oil. In some embodiments, the first and second carboxylic acids or esters pass through a bed of the metal oxide in a flow reactor. In some embodiments, the first and second carboxylic acids or esters pass through a bed of the metal oxide in a plug-flow reactor. In some embodiments, the metal oxide keeps its form (structural integrity and/or morphology) for at least about 5, about 10, about 15, about 20, about 25, about 30, about 40, about 50, about 60, about 70, about 80, about 90 or about 100 hours under the reaction condition in a provided method. In some embodiments, the first and second carboxylic acids or esters pass through a bed of the metal oxide in a plug-flow reactor. In some embodiments, the metal oxide keeps its form for at least about 5, about 10, about 15, about 20, about 25, about 30, about 40, about 50, about 60, about 70, about 80, about 90 or about 100 hours under the reaction condition in a provided method, wherein the temperature is above about 300° C. In some embodiments, the metal oxide keeps its form for at least about 5, about 10, about 15, about 20, about 25, about 30, about 40, about 50, about 60, about 70, about 80, about 90 or about 100 hours under the reaction condition in a provided method, wherein the temperature is above about 325° C. In some embodiments, the metal oxide keeps its form for at least about 5, about 10, about 15, about 20, about 25, about 30, about 40, about 50, about 60, about 70, about 80, about 90 or about 100 hours under the reaction condition in a provided method, wherein the temperature is above about 350° C. In some embodiments, the metal oxide keeps its form for at least 30 hours under the reaction condition in a provided method. In some embodiments, the metal oxide keeps its form for at least 30 hours at about 300° C. in the presence of the reaction substrates, products and other components in the feed composition. In some embodiments, the metal oxide keeps its form for at least 30 hours at about 325° C. in the presence of the reaction substrates, products and other components in the feed composition. In some embodiments, the metal oxide keeps its form for at least 30 hours at about 350° C. in the presence of the reaction substrates, products and other components in the feed composition.

Methods of the present invention typically employ elevated temperature. In some embodiments, the temperature is about 310-370° C. In some embodiments, the temperature is below about 370° C. In some embodiments, the temperature is below about 360° C. In some embodiments, the temperature is below about 350° C. In some embodiments, the temperature is below about 340° C. In some embodiments, the temperature is below about 330° C. In some embodiments, the temperature is below about 325° C. In some embodiments, the temperature is below about 320° C. In some embodiments, the temperature is below about 310° C. In some embodiments, for the upgrading of bio-oil or biofuel, wherein several components are present in addition to carboxylic acids, it is preferable to perform a provided method below 325° C. to avoid or minimize undesirable side reactions.

In some embodiments, a method of the present invention is performed at ambient pressure. In some embodiments, a method of the present invention is performed at about 1 bar. In some embodiments, a method of the present invention is performed at increased pressure. In some embodiments, a method of the present invention is performed at about 2 bar. In some embodiments, a method of the present invention is performed at about 5 bar. In some embodiments, a method of the present invention is performed at about 10 bar. In some embodiments, a method of the present invention is performed at about 20 bar. In some embodiments, a method of the present invention is performed at greater than about 2 bar. In some embodiments, a method of the present invention is performed at about greater than 5 bar. In some embodiments, a method of the present invention is performed at about greater than 10 bar. In some embodiments, a method of the present invention is performed at about greater than 20 bar.

In some embodiments, a method of the present invention is performed with the carboxylic acids or esters in the gas phase over solid catalysts under flowing reaction conditions. In some embodiments, a method of the present invention is performed in a fixed bed flow reactor. In some embodiments, the space velocity is above about 10 $g_{feed} g_{cat}^{-1} h^{-1}$. In some embodiments, the space velocity is above about 10 $g_{feed} g_{cat}^{-1} h^{-1}$, and the temperature is below about 375° C. In some embodiments, the space velocity is above about 10 $g_{feed} g_{cat}^{-1} h^{-1}$, and the temperature is below about 350° C. In some embodiments, the space velocity is above about 10 $g_{feed} g_{cat}^{-1} h^{-1}$, and the temperature is below about 325° C. In some embodiments, the space velocity is above about 15 $g_{feed} g_{cat}^{-1} h^{-1}$, and the temperature is below about 375° C. In some embodiments, the space velocity is above about 15 $g_{feed} g_{cat}^{-1} h^{-1}$, and the temperature is below about 350° C. In some embodiments, the space velocity is above about 15 $g_{feed} g_{cat}^{-1} h^{-1}$, and the temperature is below about 325° C.

In some embodiments, a provided method comprises any combination of the carboxylic acid, ester, metal oxide and/or reaction conditions described in classes and subclasses herein.

EXEMPLIFICATION

Converting carboxylic acids or esters to ketones through ketonization is an important chemical process, especially for biomass and/or fuel upgrading, including but not limited to the upgrading of biofuel and/or bio-oil. Methods using metal oxides as catalysts have been reported, however, these methods suffer from higher than desirable temperature and/or pressure, low efficiency/space velocities, and/or harsh conditions that de-stabilize the catalyst or other components in the feeding composition. Specifically, temperatures above 375° C. are needed to obtain acceptable rate at space velocities above 10. For the upgrading of bio-oil, wherein several components are present in addition to carboxylic acids/esters, it is imperative to develop methods that are able to perform conversion of acids and/or esters into ketones with high rates at lower temperatures in order to avoid the production of undesirable side reactions. In some embodiments, the present invention provides new methods for converting carboxylic acids or esters to ketones through ketonization, which solves the aforementioned problems.

We discovered that methods comprising the use of metal oxides comprising Zr, Ce, Mn and O, such as tri-metal oxide $Zr_wCe_xMn_yO_z$ with different manganese contents, are highly effective in converting acids and esters into ketones. In some embodiments, an exemplary methods provided ketonization of acetic and propanoic acids at temperature under 350° C. and space velocities about 15 $g_{feed} g_{cat}^{-1} h^{-1}$.

Catalyst Preparation

All reagents were purchased from Sigma-Aldrich. Catalysts were prepared by precipitation or co-precipitation method by using aqueous solutions of $Ce(NO_3)_3.6H_2O$ (99.5%), $ZrO(NO_3)_2$ (99%) and $Mn(NO_3)_2.6H_2O$ (99.8%) with $NH_3$ solution (25%). Exemplary procedures are described in M. Glinski, J. Kijenski, A. Jakubowski, Appl. Catal. A 128 (1995)209-217; C. A. Gaertner, J. C. Serrano-Ruiz, D. J. Braden, J. A. Dumesic, J. Catal. 266 (2009) 71-78; and C. A. Gaertner, J. C. Serrano-Ruiz, D. J. Braden, J. A. Dumesic, ChemSusChem 2 (2009)1121-1124, the content of each of which is hereby incorporated by reference.

The tri-metal oxide catalyst were prepared through a co-precipitation technique using aqueous solutions of 10 wt % dissolved metal salts in water and 3.5 wt % $NH_3$ solution. After precipitation and the aging process, the precipitate was filtrated and washed with DI water. Then the precipitate cake was dried in an air oven at 110° C. for 24 hours. The catalyst precursor was then calcined at 500° C. for four hour in a muffle furnace. Powder X-ray diffraction (PXRD) patterns revealed that all the prepared catalysts have the same morphology, confirm that the three metals in the oxide exist in a solid-phase solution.

Exemplary Procedure:

All the metal salts were dissolved in water to prepare 10 wt. % solutions, and diluted 3.5 wt. % $NH_3$ solution was also prepared. For each preparation, 400 ml in total of mixed metal salts solution with certain metal molar ratio was prepared and added to 600 ml of NH$_3$ solution in a 2000 ml glass flask with a feed rate of 5 ml/min. The flask equipped with a magnetic stirrer, a heating mantle and needed water reflux cooling system. After adding of the metal salts solution, the precipitate and the mother liquid were heated to the boiling point with continuous stirring of 400 R/min and kept for 24 hours. After precipitation and the aging process, the precipitate was filtrated and washed with DI water. Then the precipitate cake was dried in an air oven at 110° C. for 2.4 hours. The catalyst precursor was then calcined at 500° C. for 4 h in a muffle furnace (KSL, 1100X, MTI). The catalysts for further reaction tests were prepared by pressing, grinding and sieving, the catalyst particles (0.5-1 mm) were collected for further use.

Catalytic Reactions

The ketonization of carboxylic acid was carried out in a conventional fixed bed flow reactor (FIG. 1) consisting of a 12.6 mm outer-diameter Titanium tubular reactor (wall thickness 0.66 mm). The catalyst bed 5 mm in length was placed in the middle of the tubular reactor between two plugs of quartz sand and quartz wool (Sigma-Aldrich). The reactor was heated with close-fitting aluminum block heated externally by a well-insulated furnace (3210, Applied Test Systems Inc.). Temperature was measured by using a titanium coated K-type thermocouple (Omega) attached to the inside of the reactor and controlled with an 89000-10 series type temperature controller (Cole-Parmer Instrument Co.). Three mass-flow controllers (5850 Brooks Instruments) were used to control the N$_2$, CO$_2$ or other needed gas flow rates.

A HPLC pump (Acuflow series 11 pump) was used to introduce the liquid feed solution into the reactor. The effluent liquid was collected at 0° C. in an ice water bath or room temperature in a gas-liquid separator and drained for gas chromatography (GC) analysis (Agilent GC-6890) with a FID detector and (HP-1 column) and TCD detector (Carboxn 1006 plot column). Chemical identifications were performed in a GC-MS (Agilent GC-7890 with a mass spectrometer and HP-5 column), Gas phase samples were analyzed by GC TCD detector when needed.

All the gas and liquid feeds were prepared from high purity chemicals: Acetic acid (99%, Sigma-Aldrich), Acetone (99.5%, Sigma-Aldrich), Propanoic acid (Sigma-Aldrich, 99.5%), N$_2$ and CO$_2$ (UNSPSC, Air-Gas).

ZrCeMnOx catalysts were tested for acetic and propanoic acid ketonization reactions. Results at 350° C. showed that the tri-metal oxide ZrCeMn-20 (i.e. 20% Manganese content) has an activity that is 3 to 4-fold higher that the typically-used ZrCeOx catalysts under the same reaction conditions. When the reaction is performed at 310° C., the ZrCeMn-20 remains active while the ZrCeOx catalyst shows virtually no ketonization activity. Investigations revealed the presence of an intermediate carbonate species (M$_2$O$_2$CO$_3$) over the catalyst surface. Without the intention to be limiting by theory, we hypothesize that the formation of this intermediate from an Mn acetate precursor and its subsequent decomposition are central in ketonization of acetic acid.

Characterization

The specific surface area of the samples was calculated by the BET method using a nitrogen adsorption isotherm at −196° C. (Autosorb IQ). The XRD patterns of the samples were recorded on D8 (Brukerr) using CuKα radiation. Thermogravimetric analysis, TGA, was performed in a Q500 apparatus. A sequence of experiments was carried out with a fully automated and computerized SCTG system. The specimen (approximately 20 mg) was weighed into an open platinum crucible, and was heated up to 700° C. at a ramping rate of 5° C./min in nitrogen with a flow rate of 90 ml/min. ATR FTIR measurements of the solid samples were carried out with a Braden Vertex 70 equipped with ZnSe45 single crystal sample holder. High resolution TEM images were taken with a JEOL 2010 machine. The chemical identifications of the treated catalysts decomposing effluent were investigated by using pyroprobe 5100 (CDS Analytical Inc.) coupled to GC-MS. The samples were packed in an open-end quartz tube and then were rapidly heated to a desire decomposition temperature. The liberated vapors from the quartz tube were swept by a helium carrier gas stream through a heated transfer line into the inlet port of an Agilent 7890 gas chromatography (GC) equipped with an Agilent 5975 mass selective detector (MSD). A constant flow program of 0.5 mL/min and isothermal temperature of 150° C. were used for the GC column (RT-PLOT-S-bond column, Restek).

Figure 2:
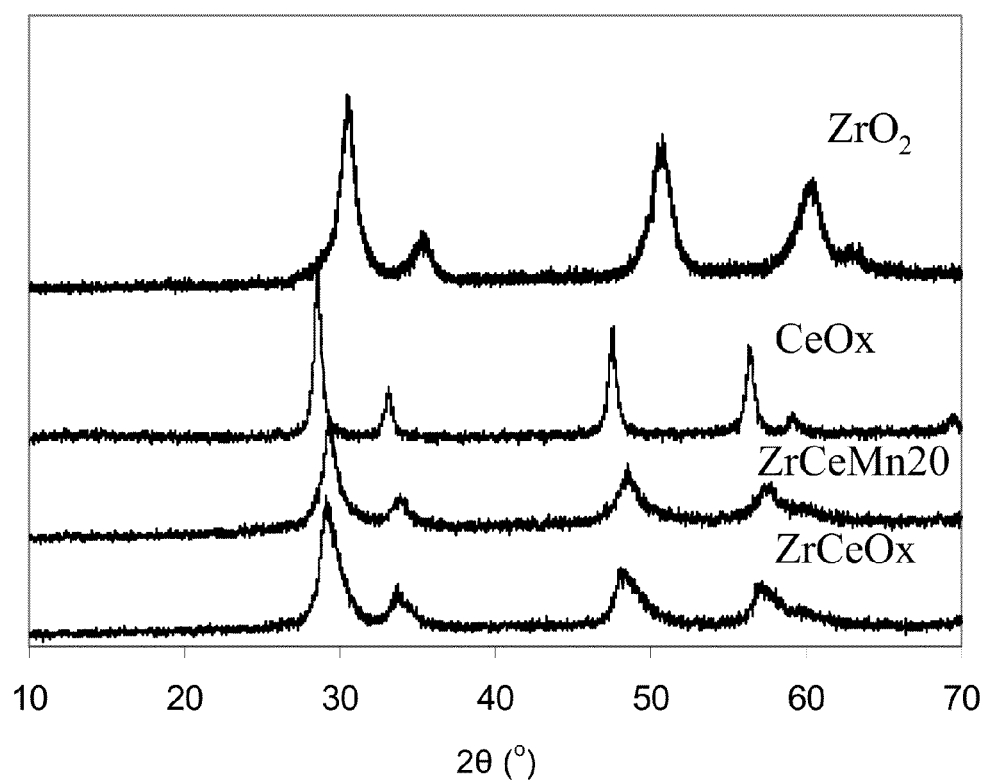
FIG. 2. XRD patterns of synthesized catalysts.
Figure 3:
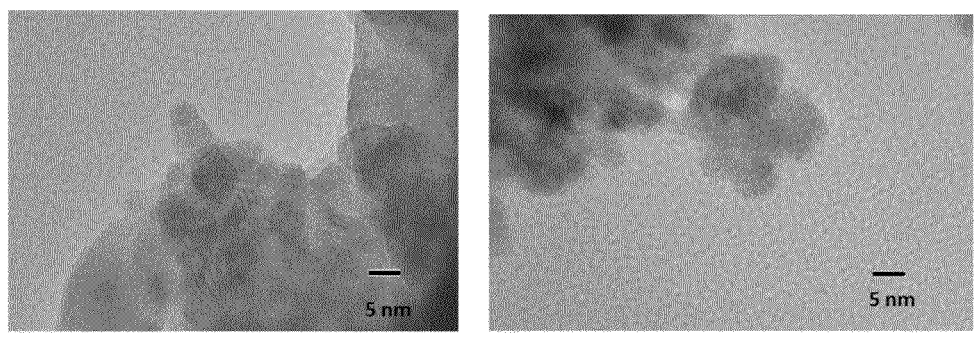
FIG. 3. TEM image of catalyst ZrCeOx (left) and ZrCeMn-20 (right).

The catalytic ketonization of acetic acid and propanoic acid to form ketones was carried out over ZrCeO, and a series of tri-metal oxide ZrCeMnO, with varying Mn content. All the prepared catalysts are listed in Table 1. The PXRD patterns of several synthesized catalysts are shown in FIG. 2, and two examples HTEM images of ZrCeO, and ZrCeMn-20 are shown in FIG. 3. The PXRD patterns show nearly identical diffractograms, which indicates that all the catalysts prepared are uniform in crystal structure and morphology. It was also verified by the TEM images that both tri-metal oxide catalysts, ZrCeMn-20 and ZrCeO$_z$, are formed as a solid solution.

TABLE 1

Prepared catalysts for ketonization of carboxylic acid.

| Catalysts* | Mn % (mol.) | Morphology | BET surface (m$^2$/g.cat) |
|---|---|---|---|
| CeO$_z$ | 0 | Tetragonal | 63 |
| ZrO$_2$ | 0 | Tetragonal | 132 |
| ZrCeO$_z$ | 0 | Tetragonal | 93 |
| ZrCeMn-5 | 5 | Tetragonal | 99 |
| ZrCeMn-10 | 10 | Tetragonal | 119 |
| ZrCeMn-20 | 20 | Tetragonal | 127 |
| ZrCeMn-40 | 40 | Tetragonal | 148 |
| CeMn-20 | 20 | Tetragonal | 101 |

*When both Zr and Ce are used for the catalysts, the mole ratios are 1:1.

The catalysts prepared have the same crystal structure. They all showed the four diffraction peaks of the tetragonal phase. From the TEM images shown in FIG. 3, it can be seen that both ZrCeOx and ZrCeMn-20 have the secondary nano-crystalline particles in the structure. The averaged particle size is around 5 nm. Without the intention to be limited by theory, this could be the reason why the ZrCeO$_z$ and ZrCeMnO, series catalysts have larger BET surface than former studies. From the XRD patterns (FIG. 2), no Mn$_2$O$_3$ were observed and the only difference of the 2θ locations can be seen of all the tetragonal phase catalysts. The (110) diffraction peak of zirconia is at 303, and 28.7 two-theta (2θ) for ceria. For ZrCeO, and ZrCeMn-20, this diffraction peak is at 29.4 and 29.8 2θ separately, exactly between the peaks location of zirconia and ceria. The powder X-ray diffraction follows the Bragg's law (Eq. 2), and the same material with a certain morphology always gives the same diffraction 2θ value because the same d value (lattice distance) and λ value (X-ray wave length). In this work, the slightly 2θ shifts were measured for the mixed metal oxides of ZrCeO$_z$ and ZrCeMn-20. For the materials with the same crystal structure, the shifts can only come from the averaged lattice distance changes. The uniformed XRD patterns show the same crystallized structure, which was also verified by the TEM images, and the averaged lattice distances.

$$2d \sin \theta = k\lambda \; (k=1,2\ldots) \tag{Eq. 2}$$

Catalytic Activity

Figure 4:
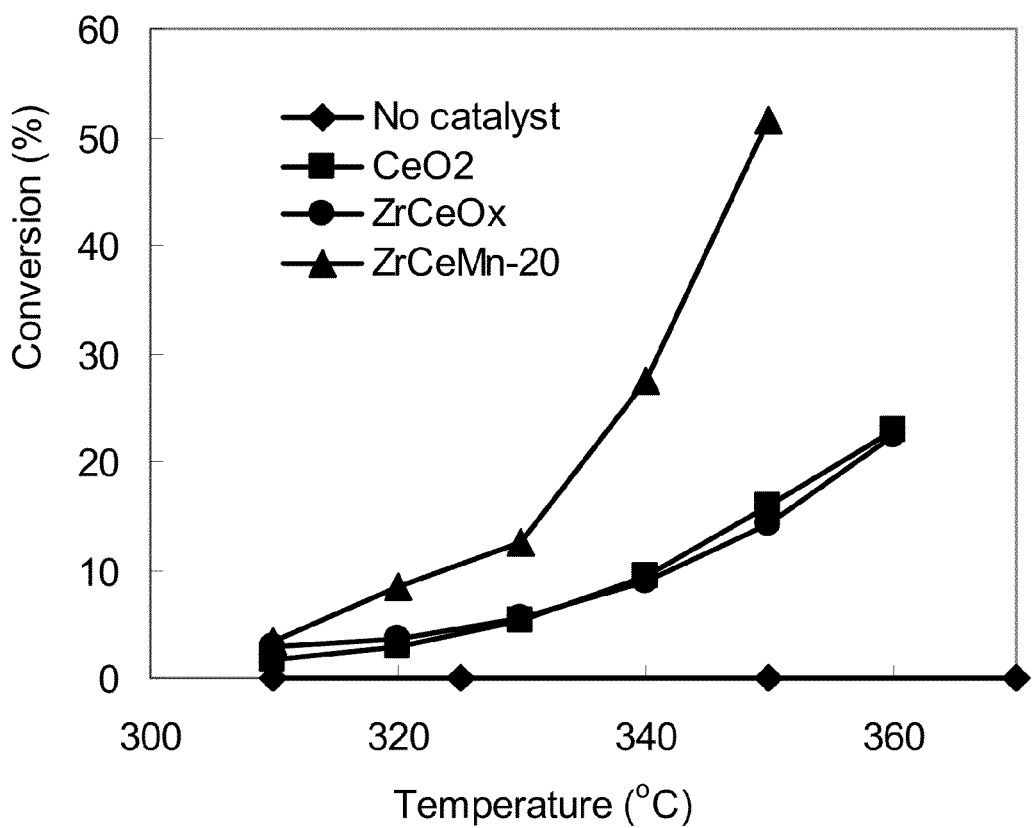
FIG. 4. Ketonization reaction of acetic acid over different catalysts. Catalyst: 1.25 g. Ti-tubing reactor (ID 11 mm), reactants: Acetic acid, 0.5 g/h [WHSV=18 g/(h.gcat.)]. Pressure: 1bar.

Experiments were carried out to determine the activities of prepared catalysts for acetic acid ketonization. FIG. 4 shows the reactant conversions of different catalysts as the function of temperatures (310° C.-370° C.). A benchmark, catalyst-free experiment was also carried out to show the activity improvement by using catalysts. For the reaction of acetic acid ketonization, only acetone, $CO_2$ and water were detected as the products by TCD and FID detectors. The conversions were used to represent the reaction activities with the same weight hourly space velocity (WHSV). It can be seen that almost no ketonization reaction happened for the benchmark experiment without catalyst. ZrCeMn-20 showed higher activities. At 350° C., ZrCeMn-20 is four times more active than $CeO_2$ and $ZrCeO_z$ and has an acetic acid conversion of 58.6%.

The blank experiment shows that no ketonization or other degradation reactions occur in the absence of benchmark experiment without catalyst. $CeO_2$ and $ZrCeO_z$ showed similar activities for acetic acid ketonization. In the presence of Mn, both CeMn-20 and ZrCeMn-20 showed high activities when compared to the same catalysts in the absence of Mn. At 350° C., ZrCeMn-20 is four times more active than $CeO_2$ and $ZrCeO_z$ and has an acetic acid conversion of 58.6%. ZrCeMn-20 is more active than CeMn-20 at 350° C. Importantly, ZrCeMn-20 shows high structural stability given that pelletized particles maintain their morphology even after 30 hours on-stream, whereas CeMn-20 particles transformed into very fine powder that increased the reactor's pressure drop. The PXRD patterns of spent catalysts of CeMn20-U350 and ZrCeMn20-U350 (i.e., used for acetic acid ketonization reaction for 30 hours at 350° C.) are shown in FIG. 4. CeMn-20 showed a peak at low 2θ that, without the intention to be limited by theory, corresponds to Ce-acetate formation, whereas ZrCeMn-20 has the same pattern as the original sample.

Reaction Kinetics Over $ZrCeMnO_z$ Catalysts

A series of experiments was carried out to exclude the influence of heat transfer and mass transfer to the reaction kinetics. And suitable WHSVs for both acetic acid and propanoic acid were selected for further kinetic studies to extract the real performance of tested catalysts. And results of catalysts activities and activation energies are listed in Table 2.

TABLE 2

Catalysts activities and activation Energies

| Catalysts | Ea (Ac) (kJ.mol$^{-1}$) | Ea (Pr) (kJ.mol$^{-1}$) | Activity (Ac) (mmol. g$^{-1}$.h$^{-1}$) (350° C.) | Activity (Pr) (mmol. g$^{-1}$.h$^{-1}$) (350° C.) |
|---|---|---|---|---|
| $ZrCeO_z$ | 143 | 129 | 44.4 | 19.1 |
| ZrCeMn-5 | 156 | 132 | 93.3 | 21.1 |
| ZrCeMn-10 | 164 | 124 | 143.7 | 24.7 |
| ZrCeMn-20 | 202 | 149 | 162.0 | 21.0 |
| ZrCeMn-40 | 167 | 149 | 136.2 | 25.9 |

From the results shown in Table 2, the magnesium content in catalyst has a direct influence to the catalytic activities and reaction activation energies of acetic acid catalytic ketonization. In the above example, the reaction activities of tri-metal oxide catalysts, ZrCeMn-A, increase with the magnesium content and reach the maximum point with ZrCeMn-20 and then drop with further increasing magnesium content.

$$\text{rate}_{ketonization} = k_{f,ketone} \cdot \frac{P^a_{acid}}{P^b_{CO_2} \cdot P^c_{H_2O} \cdot P^d_{ketone}} \quad (3)$$

Figure 5:
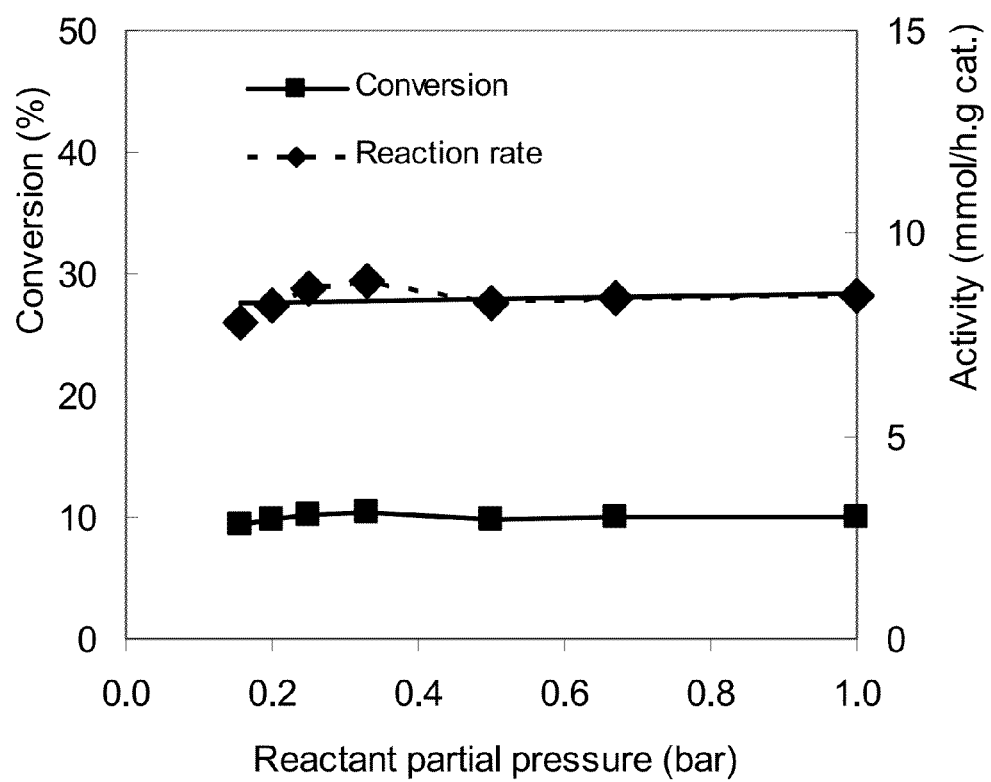
FIG. 5. The influence of acetic acid partial pressures to ketonization reaction. Catalyst: 1.25 g of ZrCeMn-20, Ti-tubing reactor (ID 11 mm), $N_2$ (50-200 ml/min.), acetic acid 6 g/h. [WHSV=4.8 g/(h.gcat.)]. Temperature: 320° C., Total Pressure: 1bar.
Figure 6:
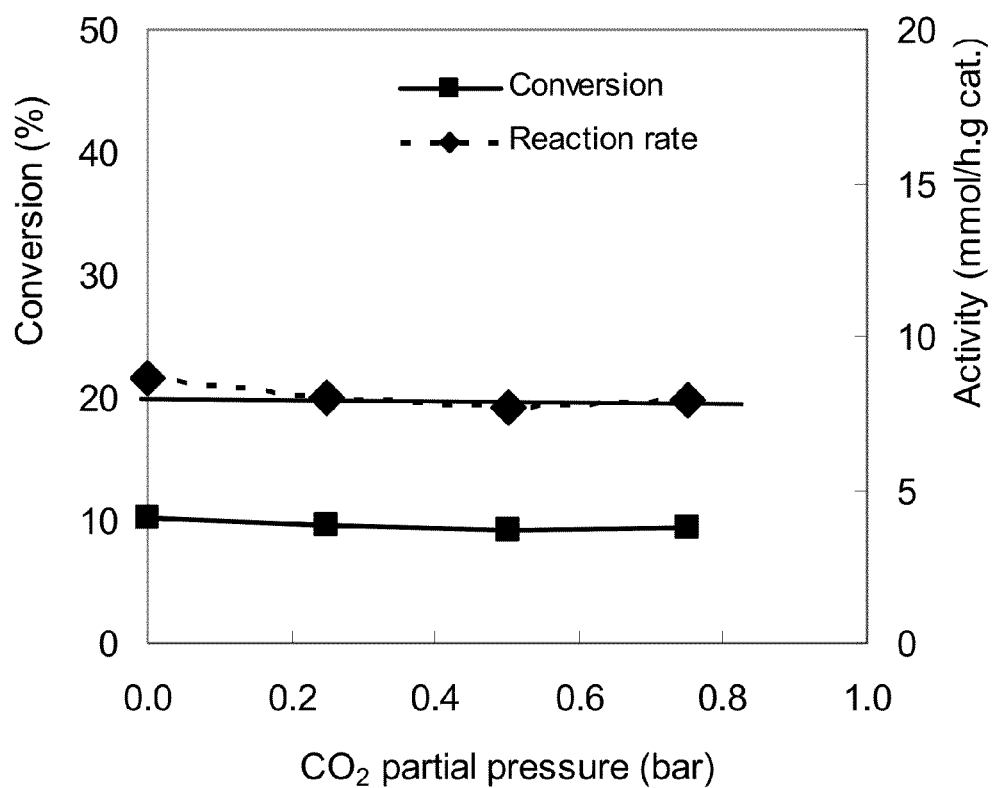
FIG. 6. The influence of $CO_2$ partial pressure to ketonization reaction. Catalyst: 1.25 g of ZrCeMn-20, Ti-tubing reactor (ID 11 mm), $CO_2$ (0-120 ml/min), acetic acid 6 g/h. [WHSV=4.8 g/(h.gcat.)]. Temperature: 320° C., Total Pressure: 1bar.
Figure 7:
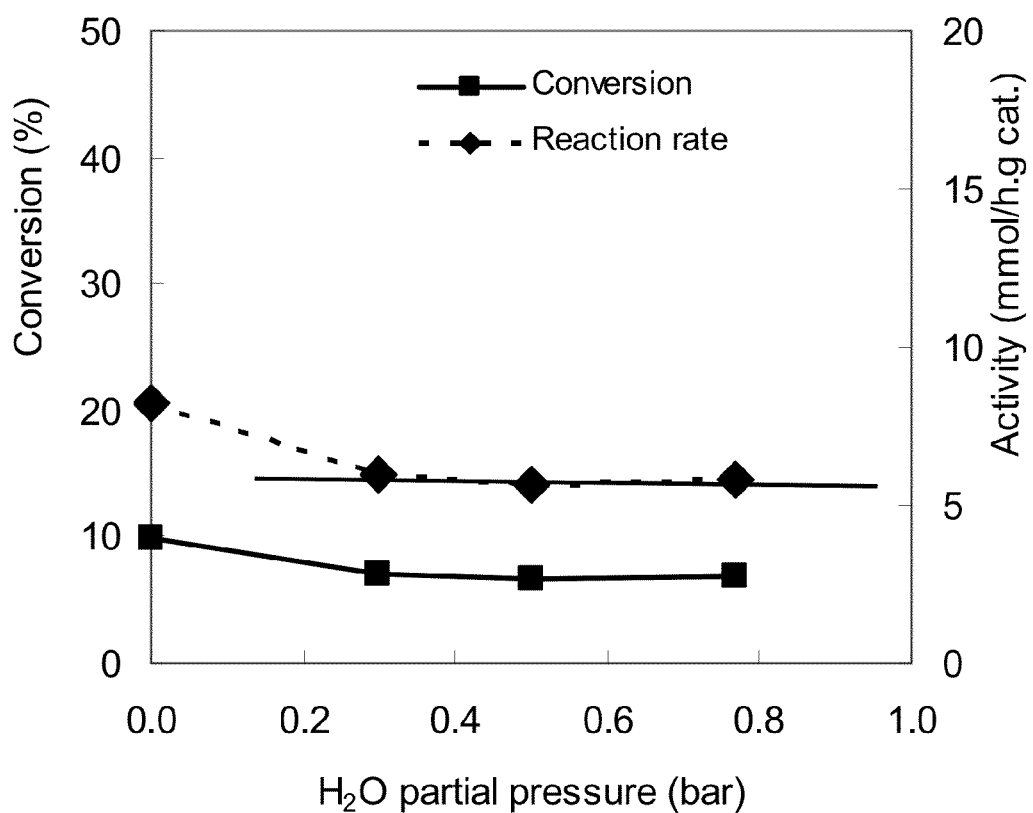
FIG. 7. The influence of $H_2O$ to ketonization reaction. Catalyst: 1.25 g of ZrCeMn-20, Ti-tubing reactor (ID 11 mm), $H_2O$ (0-6 g/h), acetic acid 6 g/h [WHSV:=4.8 g/(h.gcat.)], Temperature: 320° C., Total Pressure: 1bar.

In some embodiments, for the ketonization reaction of carboxylic acids, the rate expression can then be written as Eq. (3), where $k_{f,ketone}$ is the forward rate constant for the reaction. In some embodiments, ketones did not have an effect on the rate of catalytic ketonization reaction, and it is zero order with respect to ketone. In some embodiments, when the same WHSV acetic acid was used as reactant for reaction kinetic studies, modified reactant partial pressures were achieved by co-feed of inert gas nitrogen. The same techniques were also performed for $CO_2$ and $H_2O$ kinetic experiments. The experimental data and for the acetic acid ketonization reactions are shown in FIG. 5-7. In some embodiments, the acetic acid and $CO_2$ partial pressures have no influence on ketonization reaction over tested ZrCeMn-20 at 320° C. In some embodiments, when $H_2O$ was introduced to the system together with acetic acid, the reaction rate was de-accelerated slightly but kept almost constant with increasing $H_2O$ partial pressures. In some embodiments, all involved chemicals in the ketonization reaction has zero order rate dependence at 320° C. over ZrCeMn-20. In some embodiments, the rate expression equation can be written as Eq. (4). In some embodiments, the ketonization reaction of acetic acid over ZrCeMn-20 undergoes a route which is not determined by partial pressures of reactant and products.

$$\text{rate}_{ketonization} = k_{f,ketone} \cdot \frac{P^0_{acid}}{P^0_{CO_2} \cdot P^0_{H_2O} \cdot P^0_{ketone}} \quad (4)$$

Without the intention to be limited by theory, the lack of concentration dependence on reaction rate is indicative that the catalytic surface is dominated by a surface entity that prevents any competitive adsorption.

Reaction Mechanism of Acetic Acid Ketonization Over ZrCeMn-20

Without the intention to be limited by theory, a possible reaction mechanism is described below.

Certain experiments were carried out with acetic acid with ZrCeMn-20 to investigate reaction intermediates. The same procedure was performed as experiments mentioned before but at different temperatures. For example, 1.25 g of ZrCeMn-20 was loaded inside the Ti-tubular reactor. Pure acetic acid was feed through the catalyst bed at a flow rate of 22.5 g/h (WHSV=18) at 1 bar, the temperature was kept at 200° C. After such a reactant treatment for 5 hours, feed was switched to 50 ml/min of $N_2$ and decreased the reactor to room temperature. Then the treated catalyst ZrCeMn20-T200 was unloaded and collected, further drying at 100° C. in air oven was performed for 24 hours. Treated ZrCeMn20-T350 was also prepared but at 350° C. for comparison.

Figure 8:
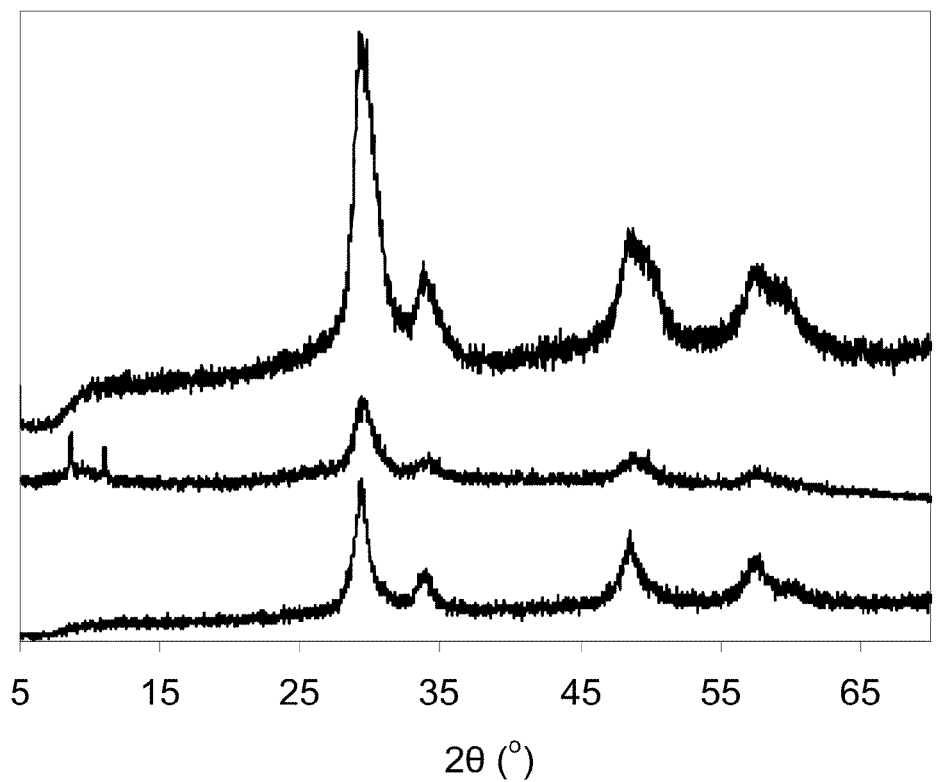
FIG. 8. XRD patterns of fresh (ZrCeMn-20) and treated catalysts with acetic acid at 200° C. (ZrCeMn20-T200) and 350° C. (ZrCeMn20-T350).
Figure 9:
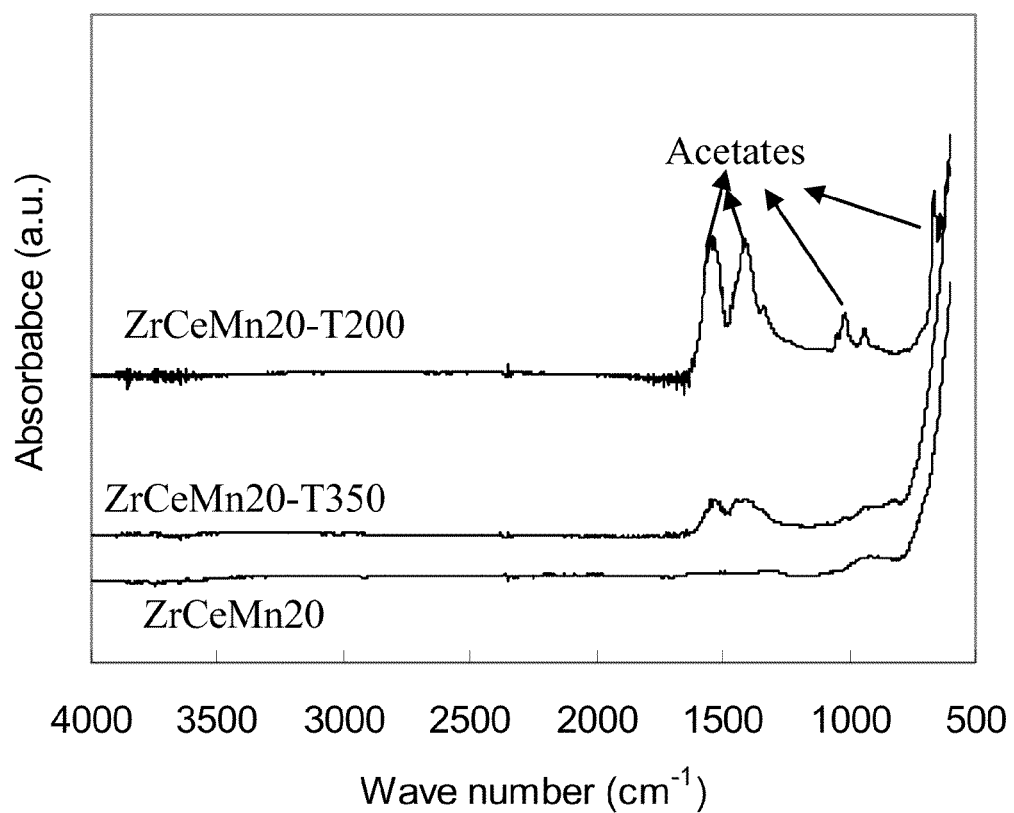
FIG. 9. Infrared spectra of fresh (ZrCeMn-20) and treated catalysts with acetic acid at 200° C. (ZrCeMn20-T200) and 350° C. (ZrCeMn20-T350).

Fresh and treated catalysts mentioned above were characterized by XRD, FT-IR, TGA and pyrolysis reactor equipped with a MS to see the difference. The XRD patterns are shown in FIG. 8 and infrared spectra are shown in FIG. 9. From the ZrCeMn20-T200 XRD pattern shown in FIG. 8, it can be seen that the catalysts' tetragonal phase remains the same as fresh catalyst but two small acetate peaks at 2θ=7.1°, 12.1° are observed after the treatment at 200° C. However, no such acetate peaks are observed with the ZrCeMn20-T350 XRD pattern. This can only be explained that the catalyst treated with acetic acid at 350° C. has no or very less acetate formed on its surface. The infrared spectra of ZrCeMn20-T200 and ZrCeMn20-T350 in FIG. 9 also show such a fact. Specifically, ZrCeMn20-T200 shows the peaks at 1402 cm$^{-1}$ and 1530 cm$^{-1}$ that correspond to —COO— asymmetric and symmetric stretching bands; peaks at 935 cm$^{-1}$ that correspond to —CO— single bond bands; and peaks at 1012 cm$^{-1}$ and 1044 cm$^{-1}$ corresponding to —$CH_3$ bending vibrations, all of which are consistent with the presence of surface acetates. Treating this sample at a higher temperature, results in the progressive decrease in intensity of these peaks and the progressive appearance of peaks assigned to the presence of surface carbonates.

Figure 10:
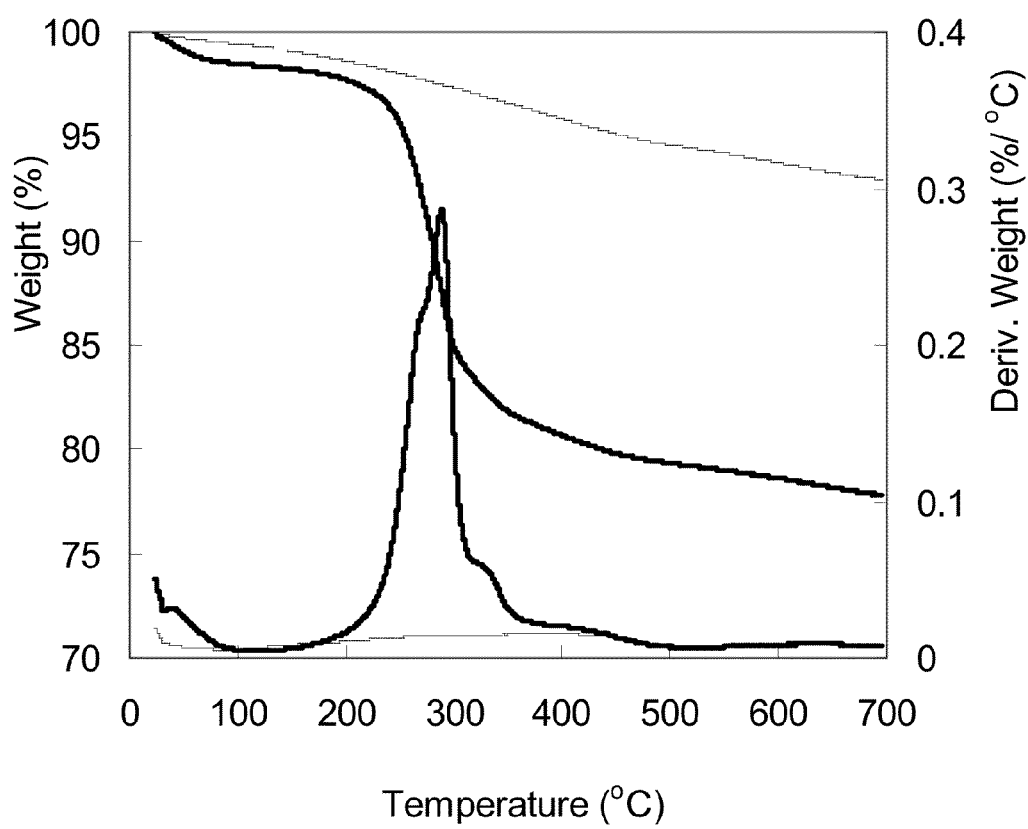
FIG. 10. TGA-DGA curves ($N_2$, 10 ml/min, 5° C./min. 25-700° C.) of treated catalysts with acetic acid at 200° C. (ZrCeMn20-T200) and 350° C. (ZrCeMn20-T350).

Further evidence was provided by thermogravimetric (TG-DTG) analyses of the samples treated at 200° C. and 350° C. (FIG. 10). The mass loss of ZrCeMn20-T200 seems to proceed through four steps. It is noted that the total weight loss of ZrCeMn20-T200 100° C. up to 600° C. is 20%, but ZrCeMn20-T350 has a weight loss of only 6%, thereby showing a drastic change in surface organic content when the sample is heated from 200° C. to 350° C.

Chemical identification of the TG effluents of ZrCeMn20-T200 and ZrCeMn20-T350 were investigated by using pyroprohe 5100 reactor (CDS Analytical Inc.) coupled with a GC-MS. In the case of ZrCeMn20-T200 acetone, $CO_2$ and trace amount of acetic acid were the detected when the temperature was fixed at 300° C. At higher temperatures only $CO_2$ was detected. In contrast, the thermal decomposition of ZrCeMn20-T350 which was treated with acetic acid at 350° C., $CO_2$ is the only detected product.

These data are consistent with the IR data showing surface acetate species for ZrCeMn20-T200 but only carbonate species for ZrCeMn20-T350. In some embodiments, the acetate over ZrCeMn20-T200 undergoes a four steps thermal decomposition exactly the same as the cerium acetate decomposition wherein weigh losses 1 and 2 of ZrCeMn20-T200 happen around 270° C. and 290° C., producing acetone and $CO_2$. Weight loss 3 from 300° C. to 370° C. produces only acetone and represents the transformation of acetate into carbonate. The weight loss 4 produces $CO_2$ and represents the decomposition of the carbonate. Without the intention to be limited by theory, the four weight loss steps of the acetate over ZrCeMn20-T200 are listed in Eq. (5-8) [M=Zr, Ce and Mn]:

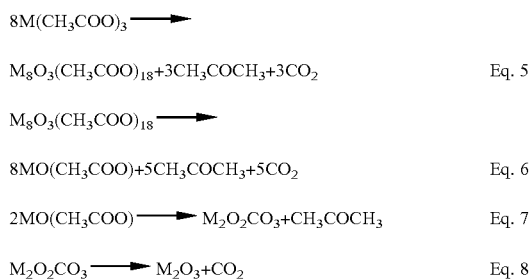

$$8M(CH_3COO)_3 \longrightarrow$$

$$M_8O_3(CH_3COO)_{18}+3CH_3COCH_3+3CO_2 \qquad \text{Eq. 5}$$

$$M_8O_3(CH_3COO)_{18} \longrightarrow$$

$$8MO(CH_3COO)+5CH_3COCH_3+5CO_2 \qquad \text{Eq. 6}$$

$$2MO(CH_3COO) \longrightarrow M_2O_2CO_3+CH_3COCH_3 \qquad \text{Eq. 7}$$

$$M_2O_2CO_3 \longrightarrow M_2O_3+CO_2 \qquad \text{Eq. 8}$$

The weigh losses 1 and 2 of ZrCeMn20-T200 happen around 270° C. and 290° C. separately and produce acetone and $CO_2$, which are represented by Eq. 5 and Eq. 6. They are too close to be separated in the TGA curves which are shown in FIG. 10, so their weight losses are taken as one weight loss in further calculations. The third step, represented by Eq. 7, happens from 300° C. to 370° C. and produces only acetone. The weight loss 4 is the decomposition of produced carbonate, represented by Eq. 8, happens after 370° C. and produces $CO_2$. The weight loss of ZrCeMn20-T350 is mainly the forth step happened over ZrCeMn20-T200 which is the carbonate decomposition represented also by Eq. 9. It has been known the total weight loss of ZrCeMn20-T200 form 100° C. up to 600° C. is 20%. Mass loss calculation for each step was made. The theoretical mass losses (1140, 3.83 and 2.77%) agreed satisfactory with the observed. TGA-DTG values (1:3.8, 3.6 and 2.6%).

Figure 11:
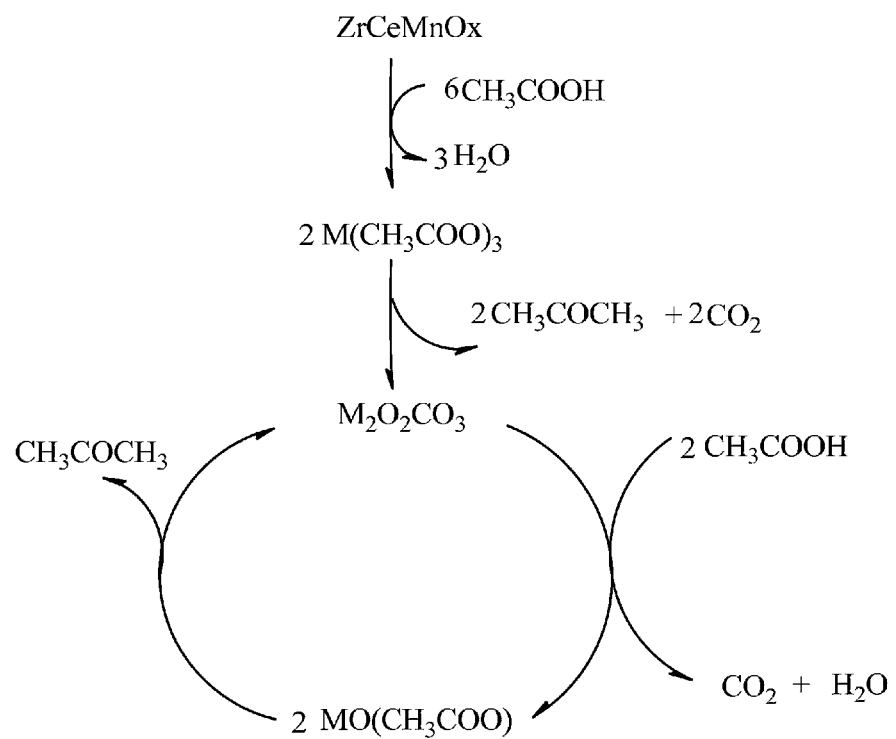
FIG. 11. Reaction diagram of acetic acid ketonization over ZrCeMn20 at 350° C.
Figure 12:
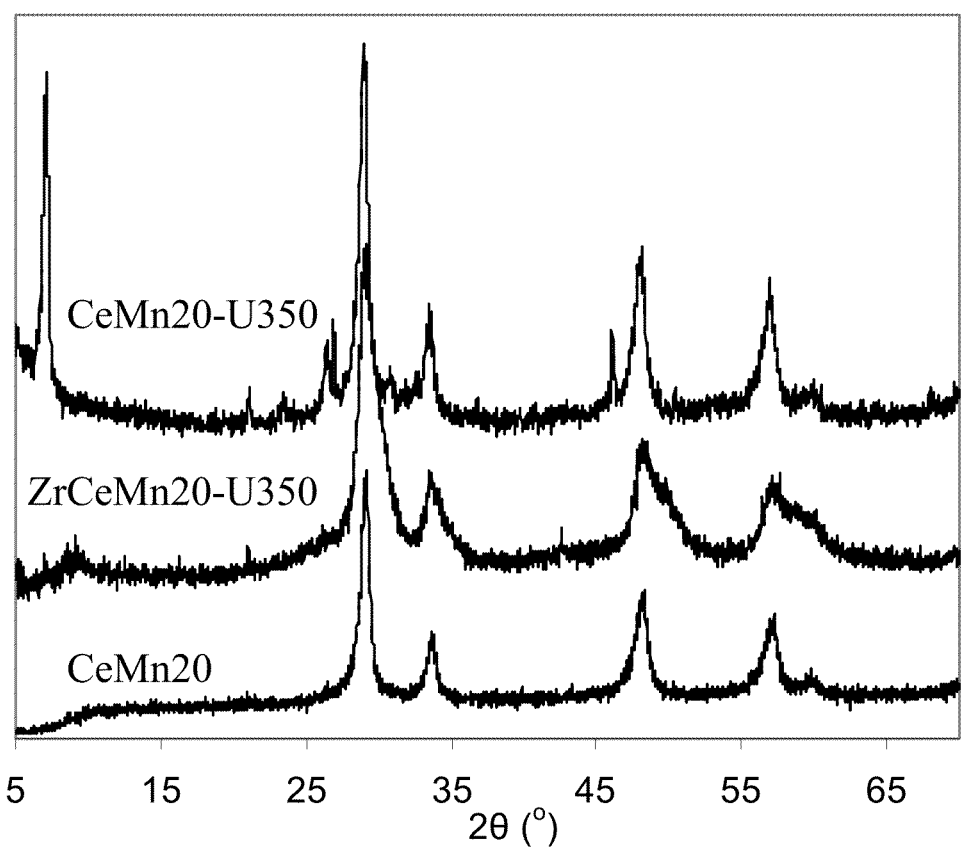
FIG. 12. XRD patterns of fresh (CeMn-20) and used catalysts CeMn20-U350 and ZrCeMn20-U350 (ketonization of acetic acid at 350° C. 20 h).

It was shown that the carbonate $M_2O_2CO_3$ is the only stable specie over ZrCeMn20 at 350° C. Without the intention to be limited by theory, in some embodiments, $M_2O_2CO_3$ is the actual catalytic specie for ketonization reaction of acetic acid over ZrCeMn20. In some embodiments, acetate and water are produced when ZrCeMn20 contact with fed acetic acid (Eq. 9). In some embodiments, $M(CH_3OO)_3$ is a semi-stable intermediate. In some embodiments, it decomposes to $MO(CH300)$ and then produce thermal stable $M_2O_2CO_3$ at reaction temperatures (300-370° C.). In some embodiments, ZrCeMn-20 works as a catalyst for acetic acid ketonization when $M_2O_2CO_3$ further reacts with acetic acid and produces $MO(CH300)$, $CO_2$ and $H_2O$ (Eq. 10). Without the intention to limited by theory, in some embodiments, the reaction mechanism of acetic acid ketonization over ZrCeMn-20 seems involve a carbonate/acetate route, and the diagram is shown in FIG. 11.

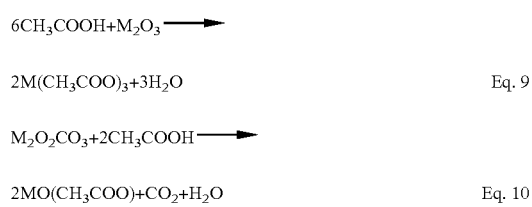

$$6CH_3COOH+M_2O_3 \longrightarrow$$

$$2M(CH_3COO)_3+3H_2O \qquad \text{Eq. 9}$$

$$M_2O_2CO_3+2CH_3COOH \longrightarrow$$

$$2MO(CH_3COO)+CO_2+H_2O \qquad \text{Eq. 10}$$

Without the intention to be limited by theory, a proposed ketonization reaction mechanism for some embodiments of acetic acid over ZrCeMn-20 under the conditions tested (300-370° C.) is depicted in FIG. 11. The cycle shows the formation of a carbonate species, $M_2O_2CO_3$, is from the decomposition of surface acetate species found in ZrCeMn20. The reaction of $M_2O_2CO_3$ with acetic acid regenerates surface acetate species with the concomitant production of $CO_2$ and water, thus closing the catalytic cycle. Given that carbonate species react readily with organic acids, without the intention to be limited by theory, it is likely that the thermal decomposition of the acetate species, $MO(CH300)$, dictates the reaction rate. This hypothesis is consistent with the observation that ketonization over ZrCeMn-20 is not influenced by the partial pressures of reactant or products.

The invention claimed is:

1. A method, comprising reacting a first carboxylic acid or ester with a second carboxylic acid or ester in the presence of a metal oxide comprising Zr, Mn and O to produce at least one ketone.

2. The method of claim 1, comprising reacting a first carboxylic acid with a second carboxylic acid in the presence of a metal oxide comprising Zr, Ce, Mn and O to produce at least one ketone.

3. The method of claim 2, wherein the first and the second carboxylic acids are the same.

4. The method of claim 3, wherein the first carboxylic acid is acetic acid or propanoic acid.

5. The method of claim 1, wherein the carboxylic acid or ester is from or in a biomass, bio-oil, fuel or biofuel.

6. The method of claim 1, wherein the metal oxide is of the formula of $Zr_wCe_xMn_yO_z$, wherein $2(w+x+y)=z$, x is 0 or a number greater than 0, and each of w, y and z is a number greater than 0.

7. The method of claim 2, wherein Zr, Ce and Mn in the metal oxide exist in a solid-phase solution.

8. The method of claim 1, wherein the metal oxide is selected from ZrCeMn-5, ZrCeMn-10, ZrCeMn-20 and ZrCeMn-40.

9. The method of claim 1, wherein the metal oxide is ZrCeMn-20.

10. The method of claim 1, wherein the metal oxide has a BET surface greater than about 100 $m^2/g$.

11. The method of claim 1, wherein the mole ratio of Zr and Ce is 1:1.

12. The method of claim 1, wherein the metal oxide is partially converted to carbonate on the surface.

13. The method of claim 1, wherein the metal oxide maintains its morphology after 30 hour at 350° C. at the presence of the first and the second carboxylic acids.

14. The method of claim 1, wherein:
the first carboxylic acid has the structure of $R^1COOH$;
the second carboxylic acid has the structure of $R^2COOH$;
the ketone has the structure of $R^1C(O)R^2$;
each of $R^1$ and $R^2$ is independently R; and
R is an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

15. The method of claim 1, wherein the space velocity is about or greater than 10 $g_{feed} g_{cat}^{-1} h^{-1}$.

16. The method of claim 15, wherein the space velocity is about 15 $g_{feed} g_{cat}^{-1} h^{-1}$.

17. The method of claim 1, wherein the ketone is produced through ketonization of the first and second carboxylic acids.

18. The method of claim 1, further comprising the presence of one or more components found in a bio-oil or fuel.

19. A method for
upgrading a fuel or bio-oil, or
converting carboxylic acids or their derivatives into ketones, or
converting a biomass,
comprising the method of claim 1.

20. The method of claim 1, wherein the metal oxide is of the formula of $Zr_wCe_xMn_yO_z$, wherein $2(w+x+y)=z$, and each of w, x, y and z is a number greater than 0.

* * * * *